(12) United States Patent
Wang et al.

(10) Patent No.: US 11,039,822 B2
(45) Date of Patent: Jun. 22, 2021

(54) LEFT ATRIAL APPENDAGE CLOSURE AND DELIVERY SYSTEM THEREOF

(71) Applicant: SHANGHAI MICROPORT MEDICAL (GROUP) CO., LTD., Shanghai (CN)

(72) Inventors: Zhen Wang, Shanghai (CN); Yi Zhou, Shanghai (CN); Yao Yao, Shanghai (CN); Junfei Li, Shanghai (CN); Qiyi Luo, Shanghai (CN); Haiyong Huang, Shanghai (CN)

(73) Assignee: SHANGHAI MICROPORT MEDICAL (GROUP) CO., LTD., Shanghai (CN)

(*) Notice: Subject to any disclaimer, the term of this patent is extended or adjusted under 35 U.S.C. 154(b) by 159 days.

(21) Appl. No.: 16/082,821

(22) PCT Filed: Mar. 16, 2017

(86) PCT No.: PCT/CN2017/076909
§ 371 (c)(1),
(2) Date: Sep. 6, 2018

(87) PCT Pub. No.: WO2017/157316
PCT Pub. Date: Sep. 21, 2017

(65) Prior Publication Data
US 2019/0117204 A1    Apr. 25, 2019

(30) Foreign Application Priority Data

Mar. 18, 2016 (CN) .......................... 201610157997.0
May 31, 2016 (CN) .......................... 201610379161.5

(51) Int. Cl.
*A61B 17/00* (2006.01)
*A61B 17/12* (2006.01)

(52) U.S. Cl.
CPC .......... *A61B 17/0057* (2013.01); *A61B 17/12* (2013.01); *A61B 17/12122* (2013.01);
(Continued)

(58) Field of Classification Search
CPC .......... A61B 17/0057; A61B 17/12022; A61B 17/12122; A61B 17/12168;
(Continued)

(56) References Cited

U.S. PATENT DOCUMENTS

2004/0093017 A1    5/2004   Chanduszko
2007/0244518 A1   10/2007   Callaghan
(Continued)

FOREIGN PATENT DOCUMENTS

CN   102612345 A   7/2012
CN   102895008 A   1/2013
(Continued)

*Primary Examiner* — Robert A Lynch
(74) *Attorney, Agent, or Firm* — Muncy, Geissler, Olds & Lowe, P.C.

(57) ABSTRACT

A left atrial appendage (LAA) closure (1) and a system (6) for delivering the LAA closure are disclosed. The LAA closure (1) includes supporting struts (11), wherein the supporting struts (11) are distributed peripherally around a first hub (10) and extend outward, the supporting strut (11) bifurcates at a first position (110) into a left branch (111) and a right branch (112). The left branch (111) of each supporting strut (11) and the right branch (112) of an adjacent supporting strut join each other at a second position (113) and extend distally to form a distal end. The LAA closure further includes a supporting rod (12) between adjacent supporting struts (11) which ensures stability, absence of irregular deformation and lateral slippage, of the LAA closure (1). With the supporting rods (12) between the adjacent supporting struts (11), the LAA closure (1) forms a dense mesh which imparts high overall strength of the LAA closure (1).

11 Claims, 13 Drawing Sheets

(52) U.S. Cl.
CPC .. *A61B 17/12168* (2013.01); *A61B 17/12172* (2013.01); *A61B 2017/00579* (2013.01); *A61B 2017/00632* (2013.01); *A61B 2017/12095* (2013.01)

(58) Field of Classification Search
CPC ...... A61B 17/12172; A61B 2017/0057; A61B 2017/00575; A61B 2017/00579; A61B 2017/00632
See application file for complete search history.

(56) References Cited

U.S. PATENT DOCUMENTS

| | | |
|---|---|---|
| 2011/0082495 A1 | 4/2011 | Ruiz |
| 2011/0208233 A1* | 8/2011 | McGuckin, Jr. ............................. A61B 17/12186 606/200 |
| 2012/0316584 A1 | 12/2012 | Miles et al. |
| 2014/0364941 A1 | 12/2014 | Edmiston et al. |
| 2015/0133989 A1 | 5/2015 | Lubock et al. |

FOREIGN PATENT DOCUMENTS

| | | |
|---|---|---|
| CN | 103099652 A | 5/2013 |
| CN | 104168843 A | 11/2014 |
| CN | 204147142 U | 2/2015 |
| CN | 104905840 A | 9/2015 |
| CN | 204971418 U | 1/2016 |
| CN | 205758647 U | 12/2016 |

* cited by examiner

LEFT ATRIAL APPENDAGE CLOSURE AND DELIVERY SYSTEM THEREOF

TECHNICAL FIELD

The present invention relates to the field of medical devices and, in particular, to a left atrial appendage (LAA) closure and a system for the delivery thereof.

BACKGROUND

Atrial fibrillation (AF) is the most common arrhythmia seen in clinical practice and has an estimated prevalence of 0.5-1.3% in the general population. Its most significant hazard is that it promotes the formation of blood clots which, when dislodged, tend to be associated with complications that may cause a significant increase in morbidity and mortality, such as stroke and occlusion of peripheral vessels. Stroke is the most common and harmful complication of AF, and there are about 15 million cases of stroke reported globally every year, in which 20% to 25% are attributed to AF. Studies show that 60% of rheumatic AF patients have their cardiogenic clots come from the left atrial appendage (LAA), and over 90% of non-valvular AF patients have their clots formed in the LAA. Therefore, preventing thromboembolism, in particular stroke, in patients with AF by LAA intervention is theoretically well-founded and of clinical significance.

Anticoagulation is currently employed as a default approach for lowering the risk of stroke in AF patients, which, however, suffers from a number of limitations. It is thus of great significance to adopt more effective and safer approaches, such as the recently popular LAA closure that is achieved by medical intervention. Commonly used LAA closures are designed either as an insert plug, such as the Watchman device, or as a disc-like plug, such as the Amplatzer Cardiac Plug (ACP).

1. Deficiencies and Disadvantages of the Insert Plug Design

A closure of the insert plug design consists of a self-expanding nickel titanium (nitinol) frame, fixation barbs around the perimeter and a polytetrafluoroethylene (PTEF) porous membrane that separates the atrium but allows the entry and exit of blood to and from the LAA.

When inserted into the LAA, a closure of this design cannot completely seal off the LAA orifice due to an irregular shape of the LAA orifice and limited deformability of the closure itself, still leaving a channel for the formation of a clot in the LAA due to AF. In addition, the LAA is a multi-lobed structure varying in shape and depth among individuals, and the closure cannot adapt to all possible LAA anatomies. Further, it suffers from insufficient anchoring.

2. Deficiencies and Disadvantages of the Disk-Like Plug Design

A closure of the disc-like plug design is a double-disk closure consisting of a lobe that anchors inside the LAA and a disk, the lobe and the disk being connected by a thinner waist. The lobe inside the LAA is configured to avoid dislocation of the device, and the disk is configured to seal off the LAA orifice.

The lobe and the disk of this closure are integral with each other and neither of them can deform completely independently of the other. As a result, after the lobe is positioned inside the LAA and the disk is buckled at the LAA orifice, the disk may not satisfactorily seal the LAA orifice under traction from the lobe and may fail to achieve a desired occlusion effect. Moreover, the lobe and the disk are both limited in lengthwise adjustability, and hence difficult to achieve a favorable anchoring and blood flow blockage effect. Again, the disk of this design is also incapable of adapting to various possible LAA anatomies.

Furthermore, the insert plug design and the disc-like plug design both suffer from insufficient strength.

In this regard, there is an urgent need in the art for a solution capable of better loading or deployment of an LAA closure.

SUMMARY OF THE INVENTION

An objective of the present invention is to propose a left atrial appendage (LAA) closure immune from the insufficient strength problem as seen in the conventional devices.

To this end, the proposed LAA closure includes a plurality of supporting struts distributed peripherally around a first hub and extending outwardly from the first hub, the supporting strut bifurcating at a first position into a left branch and a right branch, the left branch of a supporting strut and the right branch of an adjacent supporting strut joining each other at a second position and extending distally to form a distal end, the LAA closure further including a supporting rod disposed between adjacent supporting struts.

Optionally, in the LAA closure, the supporting rod may have a first end connected to the outside of the first hub, extending outwardly and bifurcating into a second end and a third end at a third position.

Optionally, in the LAA closure, the second end may be fixed between the first and second positions of the left branch of the supporting struts, and the third end may be fixed between the first and second positions of the right branch of the supporting struts.

Optionally, in the LAA closure, the second and third ends may be fixed on two adjacent supporting struts.

Optionally, in the LAA closure, a length of the supporting rod from the first hub to the third position may be smaller than a length of the supporting strut from the first hub to the first position.

Optionally, in the LAA closure, the first, second and third ends of the supporting rod may resume a Y shape.

Optionally, in the LAA closure, some or all of the supporting struts may include a barb, and/or some or all of the left and right branches may include a barb.

Optionally, in the LAA closure, the left and right branches of the same supporting strut may be connected to each other at the distal ends thereof.

Optionally, in the LAA closure, each of the distal ends may be bent toward the proximal end to form an anchor.

Optionally, in the LAA closure, a length from the point where the distal end starts bending to a final point of the distal end may be greater than a length from a junction of the distal ends to the final point.

Optionally, in the LAA closure, the distal ends may extend inwardly to form a second hub.

Optionally, in the LAA closure, the distal ends may protrude radially to form an anchor.

Optionally, in the LAA closure, the first hub may be coaxial with the second hub.

Optionally, in the LAA closure, the first and second hubs may axially protrude in the same direction or in opposite directions.

Optionally, at least a portion of the LAA closure may be covered with a biocompatible membrane.

Optionally, in the LAA closure, an angle formed between adjacent supporting struts may be 45°.

In the proposed LAA closure, the plurality of supporting struts are distributed peripherally around a first hub and extend outwardly from the first hub. Each supporting strut bifurcates at a first position into left and right branches. The left branch of a supporting strut is joined with the right branch of an adjacent supporting strut at the second position. The branches further extend distally to form distal ends thereof. Adjacent supporting struts are intervened by supporting rods which ensure stability, i.e., absence of irregular deformation and lateral slippage, of the LAA closure. In particular, the supporting struts and the supporting rods between them together constitute a dense mesh which imparts high overall strength to the LAA closure. In addition, in the proposed LAA closure, the anchors are integrally formed with the self-expanding frame without requiring a separate fabrication process. The anchors can not only provide a strong anchoring effect, but can also effectively prevent dislocation of the closure due to AF. Further, as the anchors' size is not excessive, they will not damage any tissue.

It is another objective of the present invention to propose a system for delivering and deploying an LAA closure, which is capable of better loading and deployment of the LAA closure.

To this end, the proposed delivery system includes a first delivery member and a second delivery member inside the first delivery member.

The first delivery member is adapted to be engaged with or disengaged from a first hub of the LAA closure.

The second delivery member is adapted to be engaged with or disengaged from a second hub of the LAA closure.

Optionally, in the LAA closure delivery system, the first hub may be engaged with the second hub before the LAA closure is released from the system.

Optionally, the LAA closure delivery system may further include a sheath in which the first delivery member is received.

Optionally, the LAA closure delivery system may further include a stopper for fixing the first delivery member relative to the second delivery member.

Optionally, in the LAA closure delivery system, the stopper may include a clamping portion and an actuation portion, the clamping portion is configured to partially or wholly pass through slots in the first delivery member to clamp the second delivery member.

Optionally, the LAA closure delivery system may further include a handle provided at a proximal end of the first delivery member and/or at a proximal end of the second delivery member. The handle may be provided with a visible mark.

Optionally, in the LAA closure delivery system, the LAA closure may include a first portion and a second portion, the first portion has a first end connected to the first hub and a second end connected to a first end of the second portion, the second portion has a second end connected to the second hub.

Optionally, in the LAA closure delivery system, the second portion may be located inside the first portion before the LAA closure is released from the system.

Optionally, in the LAA closure delivery system, the first portion and/or the second portion may be provided with a plurality of anchors.

Optionally, in the LAA closure delivery system, the first hub may define a step at a distal end thereof on which a proximal end of the second hub is located when the first hub is engaged with the second hub.

Optionally, in the LAA closure delivery system, the first hub may include a groove at a proximal end thereof and the groove is configured to receive a distal end of the first delivery member.

Optionally, in the LAA closure delivery system, the first delivery member may be flared out at the distal end thereof.

Optionally, in the LAA closure delivery system, the first hub may be engaged with the second hub by an internal/external spline connection or a snap connection, in case of the first hub to be engaged with the second hub.

Optionally, in the LAA closure delivery system, the first delivery member may be engaged with the first hub by a threaded connection, an internal/external spline connection or a snap connection, and/or wherein the second delivery member is engaged with the second hub by a threaded connection, an internal/external spline connection or a snap connection.

In the proposed system for delivering and deploying an LAA closure, before the LAA closure is loaded, the first delivery member is coupled to the first hub of the LAA closure and the second delivery member inside the first delivery member is coupled to the second hub thereof so that the LAA closure can be crimped to allow the loading. This can avoid an excessive length of the LAA closure when it is loaded. In the deployment process, the second portion of the LAA closure with anchors is first released. At this point, repeated relocations are allowed until a suitable deployment site is reached. After that, the first and second hubs of the LAA closure are released. Therefore, the proposed system makes it possible for the LAA closure to be better loaded or deployed.

DETAILED DESCRIPTION OF PREFERRED EMBODIMENTS

Left atrial appendage (LAA) closures and systems for their delivery proposed in this invention will be described below in further detail with reference to the accompanying drawings and a few specific embodiments. Features and advantages of the invention will be more apparent from the following detailed description, and from the appended claims. It is noted that the figures are provided in a very simplified form not necessarily presented to scale, with the only intention to facilitate convenience and clarity in explaining some embodiments of the present invention. In fact, these figures generally give emphasis on different details and are accordingly drawn to different scales.

As used herein, the term "about" applies to all numeric values, whether or not explicitly indicated. In the context of a numerical value, this term generally refers to a range of numbers that one of skill in the art would consider equivalent to the recited value (i.e., having the same function or result). In many instances, the term may include numbers that are rounded to the nearest significant figure. Unless otherwise specified, the term "about" recited elsewhere herein (i.e., in the context other than numerical values) is assumed to have its ordinary and customary meaning as understood in the context of this specification and in consistency therewith.

As used herein, the terms "outward" or "outwardly" refer to a direction pointing away from an axis of the LAA closure, whether perpendicularly thereto or not, whilst the terms "inward" or "inwardly" refers to a direction pointing toward the axis, whether perpendicularly thereto or not. The terms "proximal" and "distal" are used herein to describe relationships in terms of orientation, position and direction between different elements or actions from the perspective of a physician who is operating the device. Yet without wishing to be limiting in any sense, a "proximal end" refers to an end nearer to the physician and a "distal end" to an end that first enters the body of the patient, when the device is operated normally.

As used herein and in the appended claims, the singular forms "a", "an", and "the" include plural references unless the context clearly dictates otherwise. As used herein and in the appended claims, the term "or" is generally employed in its sense including "and/or" unless the content clearly dictates otherwise.

Embodiment 1

Figure 1:
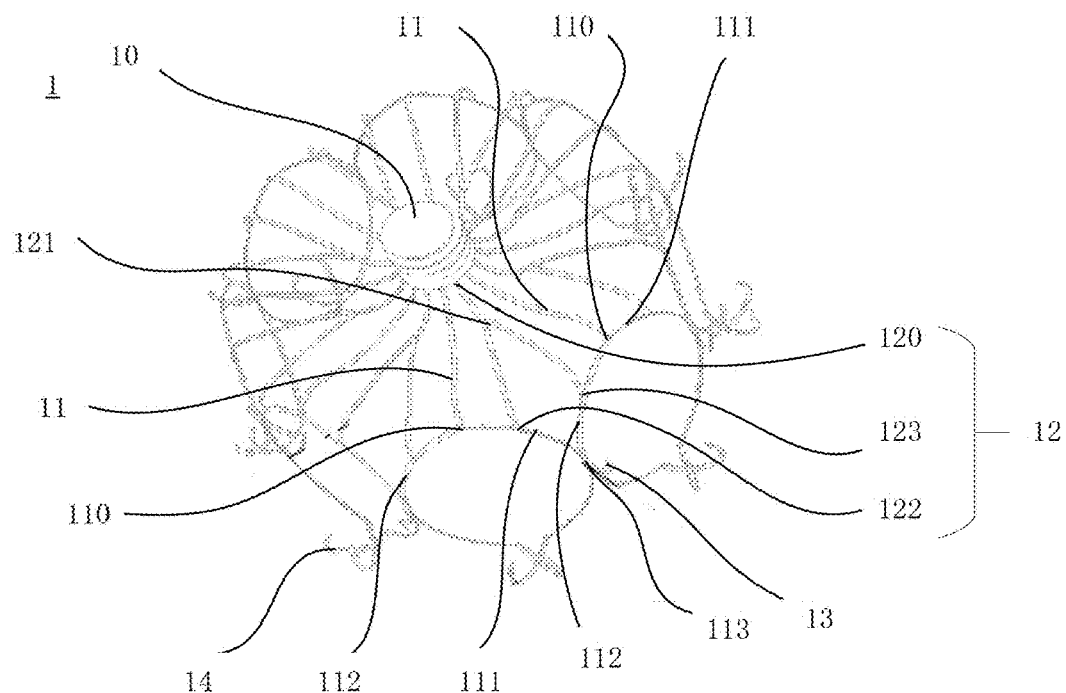
FIG. 1 is a perspective structural schematic view of a left atrial appendage (LAA) closure according to a first embodiment of the present invention.
Figure 2:
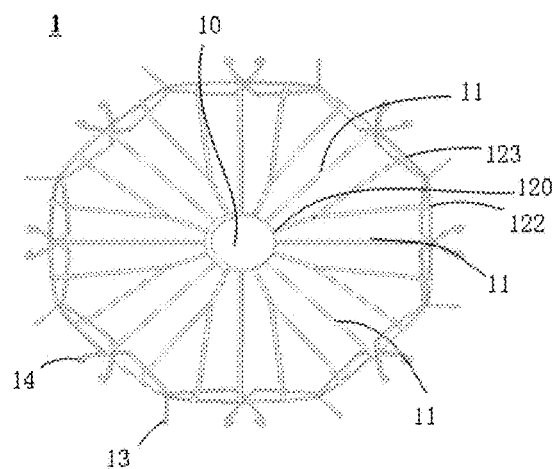
FIG. 2 is a top schematic view of the LAA closure according to the first embodiment of the present invention.
Figure 3:
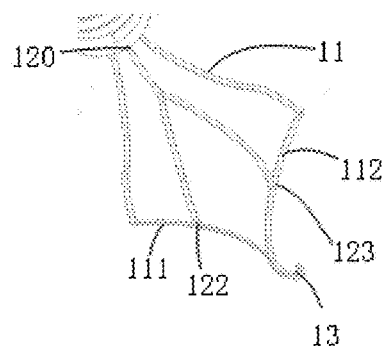
FIG. 3 is a partially enlarged schematic view of the LAA closure according to the first embodiment of the present invention.

Reference is now made to FIGS. 1 to 3, in which FIG. 1 illustrates a perspective structural schematic view of a left atrial appendage (LAA) closure according to a first embodiment of the present invention, FIG. 2 illustrates a top schematic view of the LAA closure according to the first embodiment of the present invention, and FIG. 3 illustrates a partially enlarged schematic view of the LAA closure according to the first embodiment of the present invention. As shown in FIGS. 1 to 3, the LAA closure 1 includes a plurality of supporting struts 11. The supporting struts 11 are distributed around a first hub 10 and extend outwardly from the first hub 10. Each supporting strut 11 bifurcates at a first position 110 into a left branch 111 and a right branch 112. The left branch 111 of each supporting strut 11 is joined with the right branch 112 of an adjacent one of the supporting struts 11 at a second position 113. The branches further extend distally to form distal ends thereof. The LAA closure 1 further includes supporting rods 12 each interposed between corresponding adjacent two of the supporting struts 11. This design ensures stability, i.e., absence of irregular deformation and lateral slippage, of the LAA closure 1. In particular, with the supporting rods 12 between the supporting struts 11, the LAA closure 1 appears as a dense mesh which can further improve the overall strength of the LAA closure 1.

Preferably, each supporting strut 11 is oriented at an angle of 45° with respect to a neighboring supporting strut. That is, preferably, eight supporting struts 11 are distributed around the first hub 10. Such an angular distribution of the supporting struts 11 imparts good stability and low deformability of the LAA closure 1 while allowing it to be easily deployed or retrieved.

Specifically, with continued reference to FIGS. 1 to 3, each supporting rod 12 has a first end 120 connected to an outer side of the first hub 10. Each supporting rod 12 extends outwardly from the first end 120 and bifurcates at a third position 121 into branches terminating respectively at a second end 122 and a third end 123. The second end 122 is fixed on the left branch 111 at a location between the first and second positions 110, 113, and the third end 123 is fixed on the right branch 112 at a location between the first and second positions 110, 113. Each pair of second end 122 and third end 123 are fixed on adjacent two of the supporting struts 11.

In other words, in this embodiment, each supporting rod 12 provides a certain support to corresponding adjacent two of the supporting struts 11, resulting in a further increase in the stability of the LAA closure 1 and, in particular, facilitating the avoidance of its irregular deformation and lateral slippage.

Additionally, the section of each supporting rod 12 between the first hub 10 and the third position 121 is shorter than the section of each supporting strut 11 between the first hub 10 and the first position 110. This can make the supporting rod 12 more stable, enabling a better support for the corresponding supporting struts 11.

Preferably, the supporting rod 12 terminating at the three ends, i.e., the first end 120, the second end 122 and the third end 123, resumes a Y shape. That is to say, the first end 120, the second end 122 and the third end 123 of the supporting rod 12 constitute a symmetrical structure. The Y shape is excellent in stability and reliability, so that the supporting rod 12 is excellent in stability and reliability. Further, the third position 121 is located on the supporting rod 12 at a location between one fifth to four fifth of a radial length of the supporting rod 12. This is favorable to the formation of the supporting rod 12 by cutting a tube as well as to its subsequent expansion to a stable final shape.

With continued reference to FIGS. 1 to 3, in this embodiment, some or all of the supporting struts 11 each have a barb 13, and/or some or all of the left and right branches 111, 112 each have a barb 13. These barbs 13 can facilitate the attachment of the closure 1 to the LAA. Preferably, the barbs 13 are cut from the same single piece as the supporting struts 11, the left branches 111 and/or the right branches 112. This enables a simple fabrication process and high structural reliability.

As shown in FIG. 1, in this embodiment, the left branch 111 and the right branch 112 of the same supporting strut 11 are connected to each other at their distal ends. This can enhance the circumferential stability of the supporting strut 11 and hence the stability and reliability of the LAA closure 1.

Figure 4:
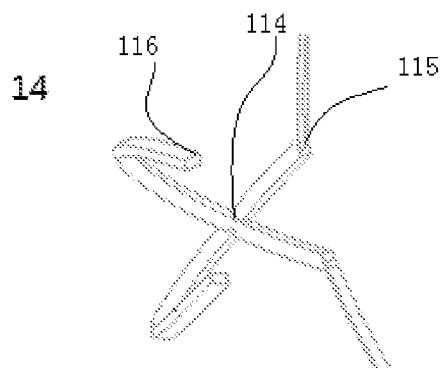
FIG. 4 is another partially enlarged schematic view of the LAA closure according to the first embodiment of the present invention.

Reference is now made to FIG. 4, a partially enlarged schematic view of the LAA closure according to the first embodiment of the present invention. In this embodiment, the left branch 111 and the right branch 112 of the same supporting strut 11, after being connected at the distal ends, further extend to final points of the left branch 111 and the right branch 112. The sections of the left branch 111 and the right branch 112 extending from the final points to the distal ends are curved over back to point proximally and hence each define an anchor 14. The anchor 14 enables firm attachment of the LAA closure 1 to the LAA.

Preferably, with continued reference to FIG. 4, for each of the left branch and the right branch, the section between a bending point 115 and the final point 116 is longer than the section between the distal end junction 114 and the final point 116. Thus, the anchor 14 has a large degree of curvature and is reinforced with the distal end junction 114. As a result, the anchor 14 is more structurally stable and can more firmly hook onto the LAA, improving the attachment of the LAA closure 1 to the LAA. Preferably, the section between the distal end junction 114 and the final point 116 has a length ranging from 1 mm to 3 mm, and the section extending from the bending point 115 to the distal end junction 114 has a length that is smaller than 3 mm.

According to this embodiment, as the anchor is defined downstream of the distal ends of the left and right branches 111, 112, i.e., terminating at the distal end junction 114, an excessive length that may cause the anchor to pierce the heart tissue, or any damage to the LAA incurred by the anchor, can be prevented.

According to this embodiment, the LAA closure 1 may be formed in one integral piece. In particular, its components including the first hub 10, the supporting struts 11, the supporting rods 12 and the anchors 14 may be formed by cutting a single tube. The integration enables a simple fabrication process and savings in manpower, materials and other economic costs.

Further, the LAA closure 1 may be at least partially covered with a biocompatible membrane.

Described below is how the LAA closure 1 can be used.

The LAA closure is advanced by a pusher through a route created with a catheter to a distal end of the catheter and to be deployed from the distal end. During the deployment, the LAA closure 1 is released from a sheath, so as to position and attach the anchors to the wall of the LAA. After that, the supporting struts 11 and the supporting rods 12 are caused to expand to sufficiently abut and adhere to the LAA wall, thereby best occluding the LAA. In order to retrieve the closure, reverse operations may be performed to cause natural detachment of the anchors from the LAA wall.

Figure 5:
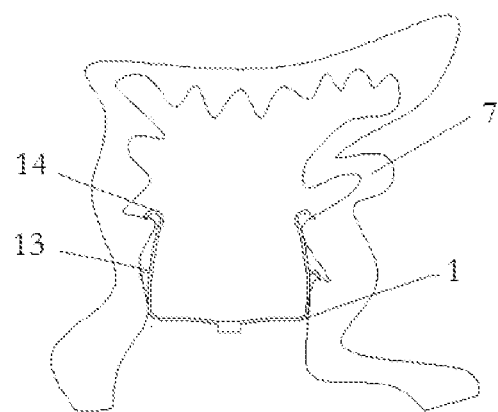
FIG. 5 is a diagrammatical view of the LAA closure according to the first embodiment of the present invention deployed within the LAA.

Specifically, reference can be made to FIG. 5, which illustrates a diagrammatical view of the LAA closure according to the first embodiment of the present invention deployed within the LAA. After the LAA closure 1 is deployed into the LAA 7, the LAA closure 1 is in an expanded configuration with the barbs 13 and the anchors 14 attached to the LAA 7.

Embodiment 2

Figure 6:
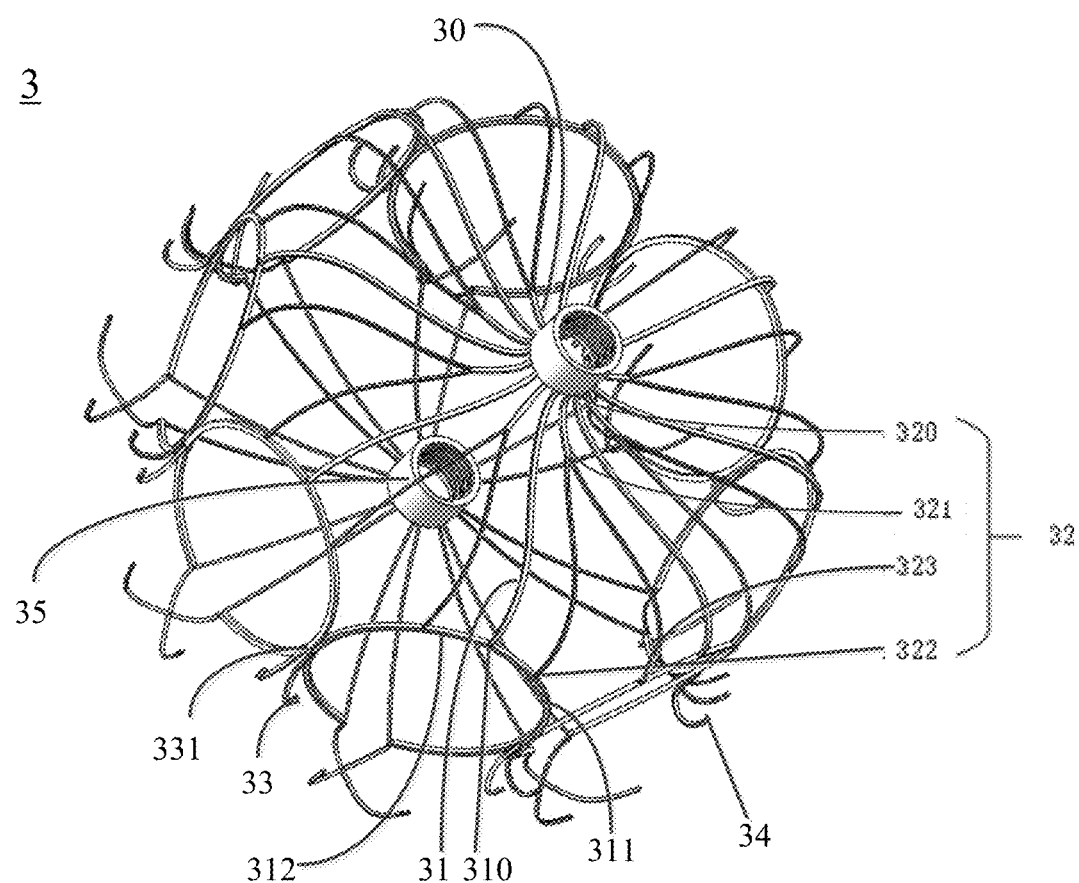
FIG. 6 is a perspective structural schematic view of an LAA closure according to a second embodiment of the present invention.
Figure 7:
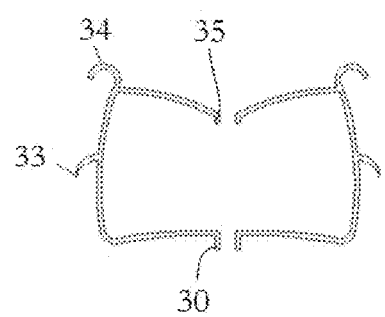
FIG. 7 is a cutaway schematic view of the LAA closure according to the second embodiment of the present invention.

Reference is now made to FIGS. 6 and 7, in which FIG. 6 illustrates a perspective structural schematic view of an LAA closure according to a second embodiment of the present invention and FIG. 7 illustrates a cutaway schematic view of the LAA closure according to the second embodiment of the present invention. As shown in FIGS. 6 and 7, the LAA closure 3 includes a plurality of supporting struts 31. The supporting struts 31 are distributed around a first hub 30 and extend outwardly from the first hub 30. Each supporting strut 31 bifurcates at a first position 310 into a left branch 311 and a right branch 312. The left branch 311 of each supporting strut 31 is joined with the right branch 312 of an adjacent one of the supporting struts 31 at a second position 313. The branches further extend distally to form distal ends thereof. The LAA closure 3 further includes supporting rods 32 each interposed between corresponding adjacent two of the supporting struts 31.

Additionally, each supporting rod 32 has a first end 320 connected to an outer side of the first hub 30. Each supporting rod 32 extends outwardly from the first end 320 and bifurcates at a third position 321 into branches terminating respectively at a second end 322 and a third end 323. The second end 322 is fixed on the left branch 311 at a location between the first and second positions 310, 313, and the third end 323 is fixed on the right branch 312 at a location between the first and second positions 310, 313. Each pair of the second end 322 and third end 323 are fixed on adjacent two of the supporting struts 31.

Some or all of the supporting struts 31 each have a barb 33, and/or some or all of the left and right branches 311, 312 each have a barb 33. The left branch 311 and the right branch 312 of the same supporting strut 31 are connected to each other at their distal ends. The distal ends of the left branch 311 and the right branch 312 bent over back to point proximally and hence define an anchor 34.

The structure described above is identical to that of the first embodiment, and a detailed description is therefore deemed unnecessary.

The second embodiment differs from the first embodiment in that the LAA closure 3 further includes a second hub 35. Specifically, the distal ends extend inwardly to form a second hub 35. With continued reference to FIG. 6, in particular, distal ends of all the left and right branches 311, 312 extend inwardly to form the second hub 35. Additionally, the first hub 30 may be coaxial with the second hub 35. This imparts good symmetry to the LAA closure 3, which is favorable to its deployment and retrieval.

Described below is how the LAA closure 3 can be used.

The LAA closure is advanced by a pusher through a route created with a catheter to a distal end of the catheter and then released from a sheath in which it is loaded. During the deployment, the LAA closure 3 is released from the sheath, the anchors attach to the wall of the LAA first and the supporting struts 31 and the supporting rods 32 then expand to sufficiently abut and adhere to the LAA wall, thereby best occluding the LAA. In order to retrieve the device, reverse operations may be performed to cause natural detachment of the anchors from the LAA wall. According to this embodiment, with the inward extensions proximally projecting from the distal ends and terminating at the second hub 35, the LAA closure 3 can be better deployed and retrieved.

Figure 8:
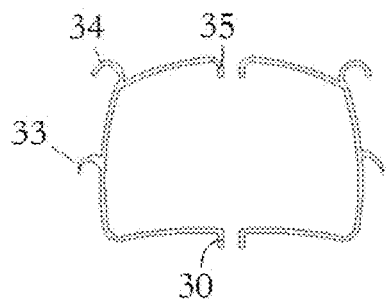
FIG. 8 is a cutaway schematic view of the LAA closure according to the second embodiment of the present invention in another configuration.
Figure 9:
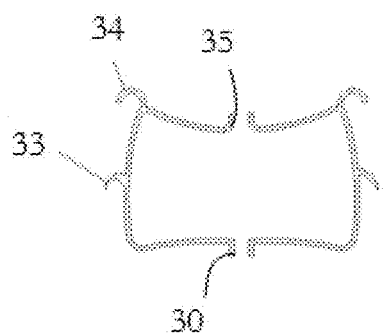
FIG. 9 is a cutaway schematic view of the LAA closure according to the second embodiment of the present invention in still another configuration.

In the second embodiment, the distal ends are described to extend proximally to form the second hub 35. In other embodiments, the distal ends may also extend distally to form the second hub 35, as shown in FIG. 8. In both of the foregoing cases, the first hub 30 and the second hub 35 are illustrated as protruding in the same direction. While in other embodiments of the present invention, the first hub 30 and the second hub 35 may also protrude in opposite directions, as shown in FIG. 9.

Embodiment 3

Figure 10:
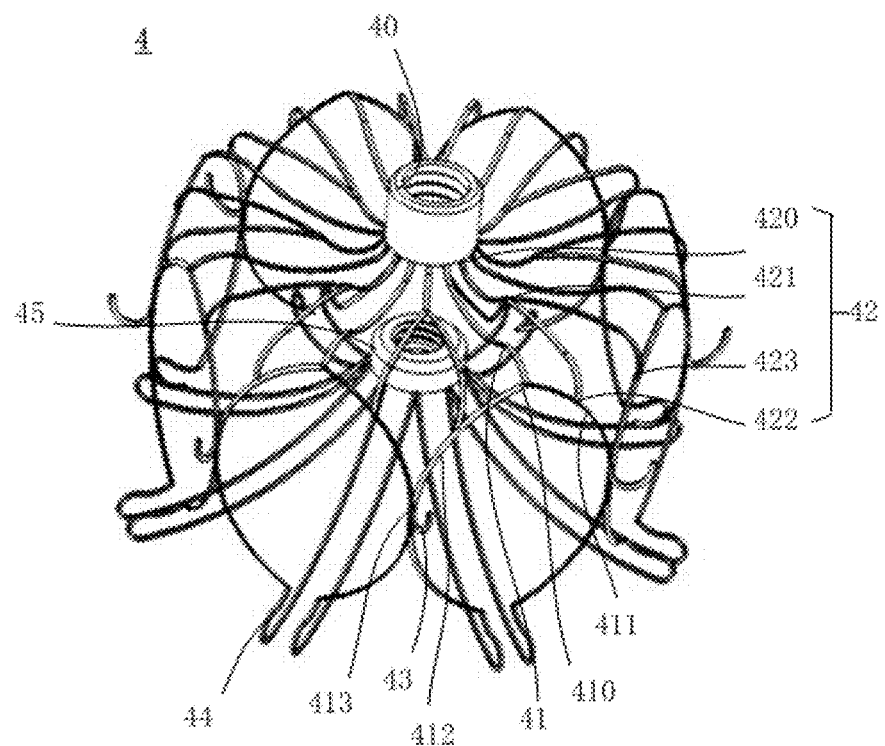
FIG. 10 is a perspective structural schematic view of an LAA closure according to a third embodiment of the present invention.

FIG. 10 is a perspective structural schematic view of an LAA closure according to a third embodiment of the present invention. As shown in FIG. 10, the LAA closure 4 includes a plurality of supporting struts 41. The supporting struts 41 are distributed around a first hub 40 and extend outwardly from the first hub 40. Each supporting strut 41 bifurcates at a first position 410 into a left branch 411 and a right branch 412. The left branch 411 of each supporting strut 41 is joined with the right branch 412 of an adjacent one of the supporting struts 41 at a second position 413. The branches further extend distally to form distal ends thereof. The LAA closure 4 further includes supporting rods 42 each interposed between corresponding adjacent two of the supporting struts 41. Extensions projecting inwardly from the distal ends terminate at a second hub 45.

In addition, each supporting rod 42 has a first end 420 connected to an outer side of the first hub 40. Each supporting rod 42 extends outwardly from the first end 420 and bifurcates at a third position 421 into branches terminating respectively at a second end 422 and a third end 423. The second end 422 is fixed on the left branch 411 at a location between the first and second positions 410, 413, and the third end 423 is fixed on the right branch 412 at a location between the first and second positions 410, 413. Each pair of the second end 422 and third end 423 are fixed on adjacent two of the supporting struts 41.

Some or all of the supporting struts 41 each have a barb 43, and/or some or all of the left and right branches 411, 412 each have a barb 43.

The third embodiment differs from the second embodiment in that the left branch 411 and the right branch 412 of the same supporting strut 41 are curved at their distal ends to define anchors 44 without joining with each other at their distal ends. Such anchors 44 according to this embodiment also allow firm attachment of the LAA closure 4 to the LAA.

Embodiment 4

Figure 11:
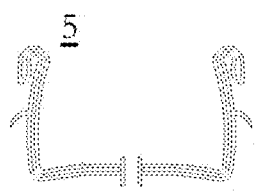
FIG. 11 is a cutaway schematic view of an LAA closure according to a fourth embodiment of the present invention.

FIG. 11 is a cutaway schematic view of an LAA closure according to a fourth embodiment of the present invention. The fourth embodiment is essentially identical in structure to the first embodiment except that the supporting struts and supporting rods in this embodiment are double-layered nickel titanium (nitinol) components, which impart higher quality and stability to the LAA closure 5.

In each of the LAA closures according to the second and third embodiments, the first and second hubs and the components connecting them together (i.e., the supporting struts and the supporting rods, which form a dense mesh) together form a structure resembling a closed cage. Hereinafter, such devices are thus referred to closed cage-like LAA closures.

Figure 12:
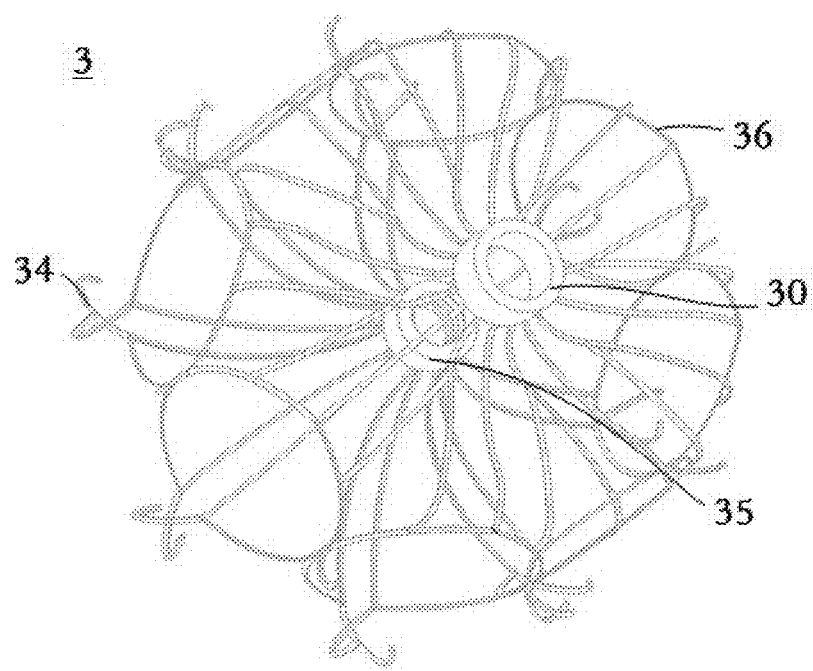
FIG. 12 is a structural schematic of an LAA closure suited to be delivered by a delivery system according to a fifth embodiment of the present invention.

With such a closed cage-like LAA closure as shown in FIG. 12 as an example, a detailed description will be given below about how systems for delivering the LAA closure are structured and work. The LAA closure of FIG. 12 may be the same as or similar to that of FIG. 6 according to the second embodiment, and a perspective structural schematic view of it is shown in FIG. 12 in which, for the sake of simplicity, only the first hub 30, the anchors 34, the second hub 35 and the cage-like structure 36 are indicated. As shown in FIG. 12, the LAA closure 3 includes the first hub 30, the second hub 35 and the cage-like structure 36 that connects the first hub 30 and the second hub 35 together. The anchors 34 are formed on the cage-like structure 36. Preferably, the anchors 34 may be distributed on the cage-like structure 36 in multiple rows, thus enabling easier attachment of the LAA closure 3 to the LAA with higher stability and reliability.

It is noted that the closed cage-like LAA closure may also assume one of configurations other than as shown, which are also suitable for the delivery by the system. In addition, apart from the most typical cage-like structure, the LAA closure may also be otherwise constructed without departing from the scope of the present invention.

Embodiment 5

Figure 13:
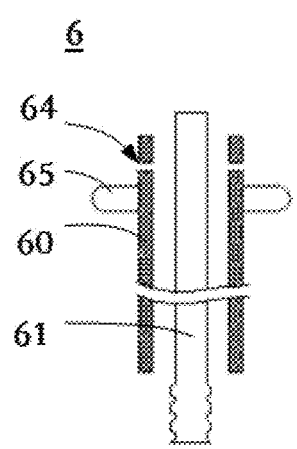
FIG. 13 is a structural schematic of a system for delivering the LAA closure according to the fifth embodiment of the present invention.

FIG. 13 is a structural schematic of a system for delivering the LAA closure according to a fifth embodiment of the present invention. As shown FIG. 13, the system 6 includes a first delivery member 60 and a second delivery member 61 inside the first delivery member 60. The first delivery member 60 may be coupled to or separated from the first hub 30 (of the LAA closure 3), and the second delivery member 61 may be coupled to or separated from the second hub 35 (of the LAA closure 3). Specifically, in order to load the LAA closure 3, the first delivery member 60 is coupled to the first hub 30 of the LAA closure 3 and the second delivery member 61 is coupled to the second hub 35 of the LAA closure 3 so that the LAA closure 3 can be crimped to allow the loading. This design can avoid an excessive length of the LAA closure 3 when it is loaded.

Figure 14:
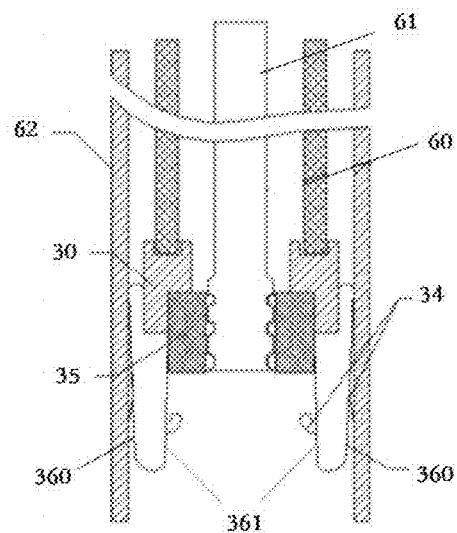
FIG. 14 schematically illustrates the system according to the fifth embodiment of the present invention prior to the deployment of the LAA closure.

Reference is now made to FIG. 14, a schematic illustration of the system according to this embodiment before the LAA closure is deployed. As shown in FIG. 14, in this embodiment, the system 6 further include a sheath 62. The first delivery member 60 is loaded inside the sheath 62. Additionally, before the LAA closure 3 is deployed from the system 6, the first delivery member 60 is coupled to the first hub 30 and the second delivery member 61 is coupled to the second hub 35. Further, the first hub 30 may be engaged with the second hub 35 so that the LAA closure 3 is crimped and has a length much smaller than that when it is loaded in the sheath 62 with the first hub 30 and the second hub 35 being separate from each other. This is even more favorable to the deployment of the LAA closure 3.

In the crimped configuration of the LAA closure 3 shown in FIG. 14, the cage-like structure 34 has a first portion 360 and a second portion 361. The first portion 360 is connected to the first hub 30 at one end and to the second portion 361 at the other end, and the other end of the second portion 361 is connected to the second hub 35. In this embodiment, several anchors 34 may be formed on each of the first portion and second portions 360, 361 of the LAA closure 3. Before the LAA closure 3 is deployed from the system 6, the second portion 361 is located internal to the first portion 360. The first portion 360 vertically overlaps the second portion 361, resulting in a significant reduction in the length of the LAA closure 3 when it is loaded in the sheath. Since the LAA closure 3 is crimped when loaded within the system 6, with the anchors 34 on the second portion 361 hidden in the interior space, they will not come into contact or scratch the sheath 62 during entry into or movement within the sheath 62.

Figure 15:
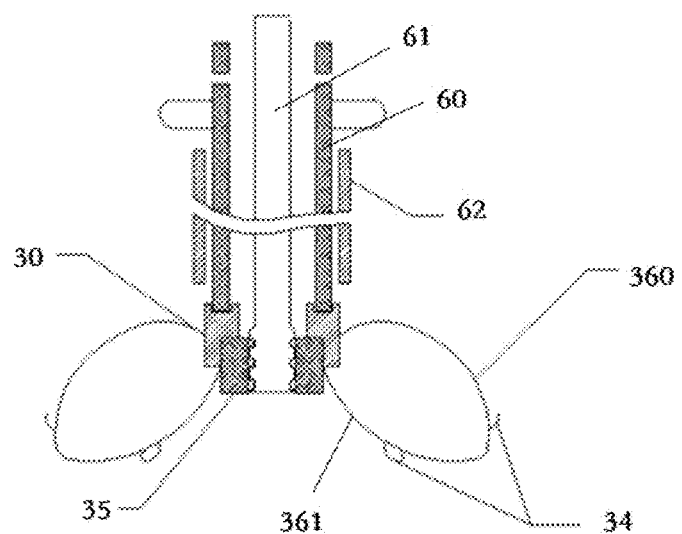
FIG. 15 schematically illustrates the system according to the fifth embodiment of the present invention, with the LAA closure being partially released.
Figure 16:
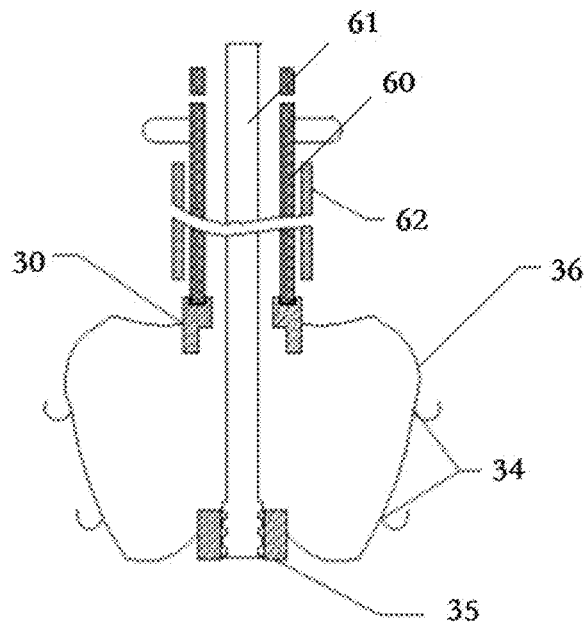
FIG. 16 schematically illustrates the system according to the fifth embodiment of the present invention in another configuration, with the LAA closure being partially released.
Figure 17:
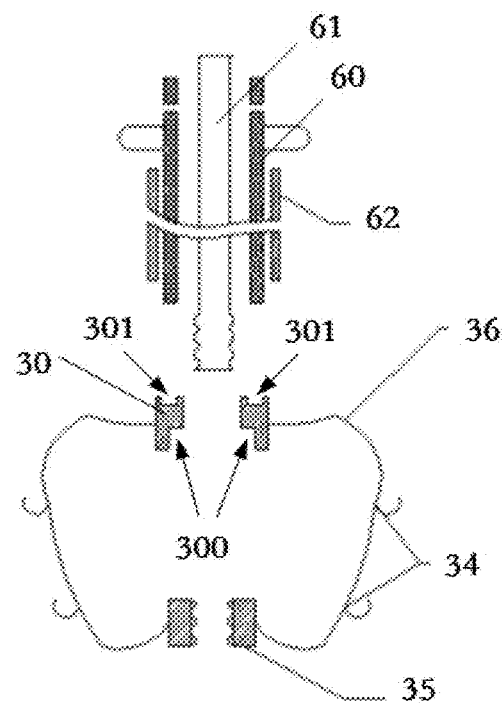
FIG. 17 schematically illustrates the system according to the fifth embodiment of the present invention subsequent to complete deployment of the LAA closure.

Reference is made further to FIGS. 15 to 17, which show how the LAA closure 3 is deployed.

At first, as shown in FIG. 15, the first delivery member 60 and the second delivery member 61 are pushed from the sheath 62 so that the LAA closure 3 (see FIGS. 6 and 12) gradually emerges from the sheath 62. Specifically, the first portion 360 of the LAA closure 3 and the anchors 34 thereon first come out of the sheath 62. At this point, the system 6 remains in connection with the LAA closure 3, i.e., the LAA closure 3 is still under control of the system 6, allowing the physician to relocate the device through changing positions of attachment of the anchors 34 to the LAA.

Subsequently, as shown in FIG. 16, the second delivery member 61 is pushed out of the sheath 62 (with the first delivery member 60 either not being pushed any longer or pushed to advance slower) until the remaining part of the LAA closure 3 leaves the sheath 62. Again, at this point, as the first and second hubs 30, 35 remain in connection with the first and second delivery members 360, 361, i.e., the LAA closure 3 remains controllable (by the physician), the physician is still capable of relocating the device through changing positions of attachment of the anchors 34 to the LAA.

Next, as shown in FIG. 17, after the LAA closure 3 has been deployed in place within the LAA, the physician may completely deploy the LAA closure 3. The deployment may in particular include: separating the second delivery member 61 from the second hub 35b; and separating the first delivery member 60 from the first hub 30. At this point, the LAA closure 3 cannot be relocated any longer.

With continued reference to FIG. 17, in this embodiment, the second delivery member 61 may be engaged with the second hub 35 by a threaded connection. Tightening or loosening the threaded connection can lead to the engagement or disengagement between the second delivery member 61 and the second hub 35. In other embodiments, the second delivery member 61 may also be otherwise engaged with the second hub 35, for example by a spline connection or a snap connection.

In this embodiment, the engagement between the first hub 30 and the second hub 35 may be accomplished by the following approach: a distal end of the first hub 30 includes a step 300, when the first hub 30 is engaged with the second hub 35, a proximal end of the second hub 35 is within the step 300. The first delivery member 60 may be coupled to the first hub 30 by inserting a distal end of the first delivery member 60 into a groove 301 defined at a proximal end of the first hub 30. This connection between the first delivery member 60 and the first hub 30 can be easily established and the disconnection between the first delivery member 60 and the first hub 30 can also be easily established during the deployment process.

Figure 18:
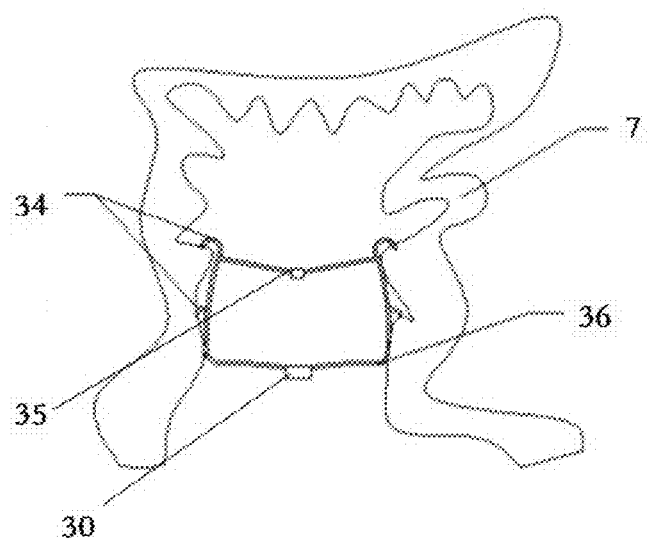
FIG. 18 schematically illustrates the system according to the fifth embodiment of the present invention, with the LAA closure being anchored within the LAA.

With the above steps completed, the LAA closure 3 will attach to and hence occlude the LAA 7 (see FIGS. 18 and 6).

Figure 19:
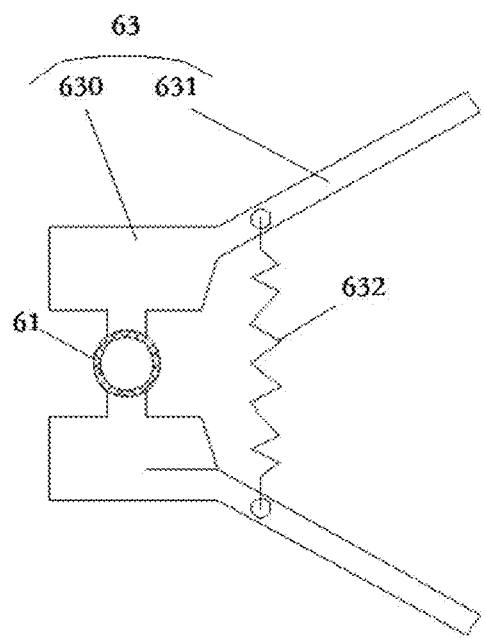
FIG. 19 is a structural schematic of a stopper according to the fifth embodiment of the present invention.
Figure 20:
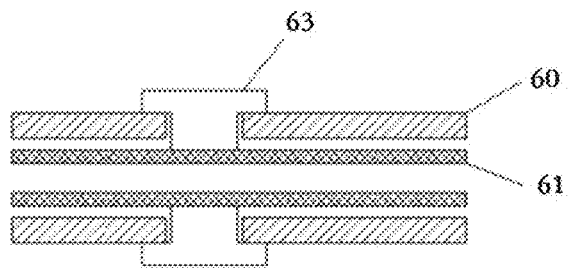
FIG. 20 schematically illustrates how the stopper according to the fifth embodiment of the present invention fixes a first delivery member relative to a second delivery member.

With additional reference to FIGS. 19 and 20, in which FIG. 19 illustrates a stopper according to the fifth embodiment of the present invention; FIG. 20 schematically illustrates how the stopper according to the fifth embodiment of the present invention fixes a first delivery member relative to a second delivery member. In the embodiment of the present invention, the system 6 may further include a stopper 63 for fixing the second delivery member 61 relative to the first delivery member 60. Specifically, the stopper 63 includes a clamping portion 630 and an actuation portion 631. The clamping portion 630 includes protrusions that can pass through slots 64 in the first delivery member 60 and clamp the second delivery member 61. The stopper 63 allows easily control the first delivery member 60 and the second delivery member 61, and hence achieve the simultaneous advancement and other operations on the first delivery member 60 and the second delivery member 61. The actuation portion 631 is provided with a spring 632 for immobilization of the clamping portion 630.

Referring back to FIG. 13, the system 6 may further includes a handle 65. In the embodiment of the present invention, the handle 65 is proposed at a proximal end of the first delivery member 60. The clamping and advancement of the handle 65 also allow easy advancement of the first and second delivery members 60, 61 within the sheath 62 and eventual deployment of the LAA closure 3. Preferably, the handle 65 is provided with a visible mark indicating rotation directions in which the threaded connection between the second delivery member 61 and the second hub 35 can be tightened or loosened to cause the engagement or disengagement between the second delivery member 61 and the second hub 35.

In this embodiment, the LAA closure 3 can be deployed as described below.

The handle 65 or the stopper 63 is manipulated to cause the first delivery member 60 and the second delivery member 61 to advance within the sheath 62 so that a first portion of the LAA closure 3 is deployed (under the distal push of the first delivery member 60 and the second delivery member 61). At this point, repeated relocations and adjustments are possible. After the first portion is deployed in place, the stopper 63 is deployed and the threaded connection between the second delivery member 61 and the second hub 35 is loosened so that the LAA closure 3 covers the LAA 7. The first delivery member 60 is then retracted to completely deploy the LAA closure 3.

In summary, the system for delivering the LAA closure according to this embodiment can avoid an excessive length of the LAA closure when it is loaded in the sheath. Meanwhile, since repeated relocations during the deployment are possible, the LAA closure can be better loaded into and deployed from the sheath.

Embodiment 6

Figure 21:
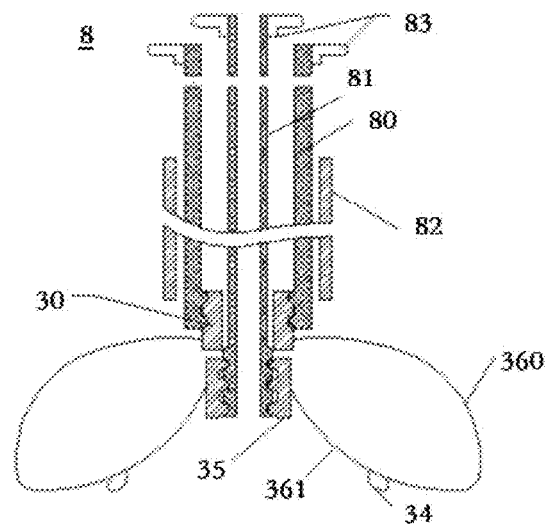
FIG. 21 schematically illustrates a system for delivering the LAA closure according to a sixth embodiment of the present invention, with the LAA closure being partially released.
Figure 22:
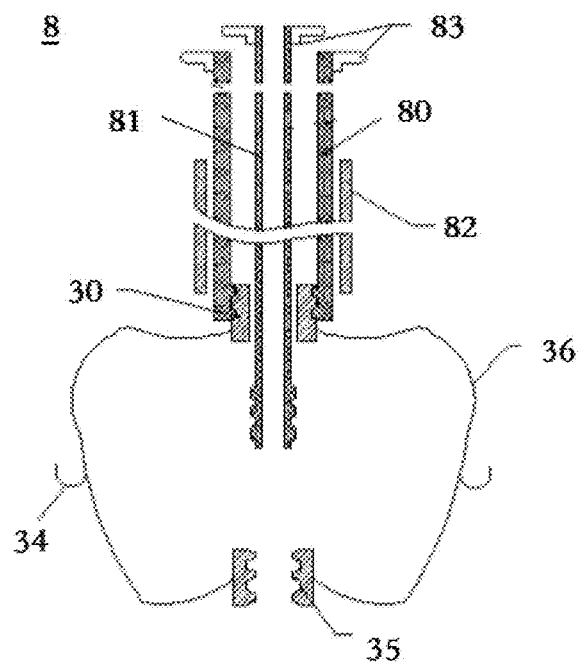
FIG. 22 also schematically illustrates the system according to the sixth embodiment of the present invention, with the LAA closure being partially released.
Figure 23:
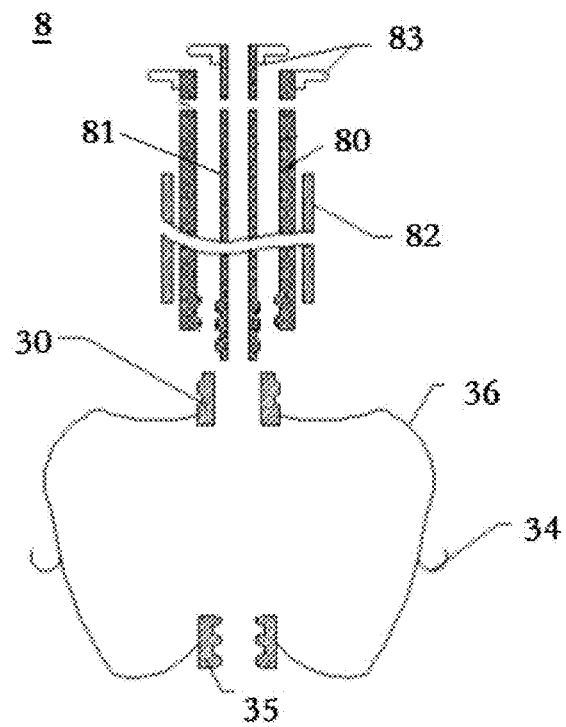
FIG. 23 schematically illustrates the system according to the sixth embodiment of the present invention subsequent to complete deployment of the LAA closure.

FIGS. 21 to 23 show a system for delivering the LAA closure according to a sixth embodiment of the present invention, with the LAA closure being partially released. As shown in these figures, the system 8 includes a first delivery member 80 and a second delivery member 81 inside the first delivery member 80. The first delivery member 80 may be coupled to or separated from the first hub 30 (of the LAA closure 3), and the second delivery member 81 may be coupled to or separated from the second hub 35 (of the LAA closure 3). Specifically, in order to load the LAA closure 3, the first delivery member 80 is coupled to the first hub 30 of the LAA closure 3 and the second delivery member 81 is coupled to the second hub 35 of the LAA closure 3 so that the LAA closure 3 can be crimped to allow the loading. This design can avoid an excessive length of the LAA closure 3 when it is loaded.

In this embodiment, the second delivery member 81 is engaged with the second hub 35 in the same manner as the first embodiment, i.e., by a threaded connection.

Differing from the first embodiment, the first delivery member 80 is also engaged with the first hub 31 by a threaded connection in this embodiment.

Further, in this embodiment, each of the first delivery member 80 and the second delivery member 81 is provided with a handle 83 at the proximal end. The handle 83 at the proximal end of the second delivery member 81 enables independent advancement of the second delivery member 81. Furthermore, each of the handles 83 of the first delivery member 80 and the second delivery member 81 may be provided with a visible mark. In this embodiment, the mark on the handle 83 at the proximal end of the first delivery member 80 indicates rotation directions in which the threaded connection between the first delivery member 80 can the first hub 31 can be tightened or loosened. Similarly, the mark on the handle 83 at the proximal end of the second delivery member 81 indicates rotation directions in which the threaded connection between the second delivery member 81 and the second hub 35 can be tightened or loosened. In this way, the first delivery member 80 and the second delivery member 81 can be easily connected to or separated from the first hub 31 and the second hub 35, respectively.

Moreover, the delivery system 8 may also include a sheath, a stopper and other components (including those not specified in this embodiment) that are the same as the first embodiment. These components will not be detailed again here, and reference can be made to the first embodiment for their details.

With continued reference to FIGS. 21 to 23, in this embodiment, the LAA closure 3 can be deployed as described below.

The handles 83 or the stopper (not shown) are/is manipulated to cause the first delivery member 80 and the second delivery member 81 to advance within the sheath 82 so that a first portion of the LAA closure 3 is deployed (under the distal push of the first delivery member 80 and the second delivery member 81). At this point, repeated relocations and adjustments are possible. After the first portion is deployed in place, the stopper is released and the threaded connection between the second delivery member 81 and the second hub 35 is loosened so that the LAA closure 3 covers the LAA 7. The threaded connection between the first delivery member 80 and the first hub 35 is then released to completely deploy the LAA closure 3.

In summary, the system for delivering the LAA closure according to this embodiment can avoid an excessive length of the LAA closure when it is loaded in the sheath. Meanwhile, since repeated relocations during the deployment are possible, the LAA closure can be better loaded into and released from the sheath.

Embodiment 7

Figure 24:
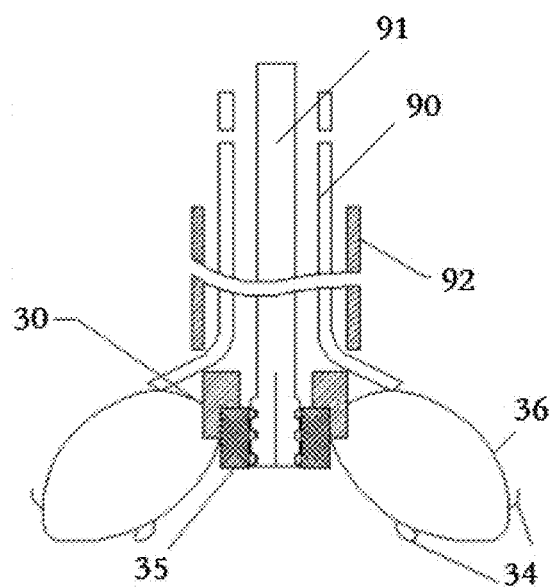
FIG. 24 schematically illustrates a system for delivering the LAA closure according to a seventh embodiment of the present invention, with the LAA closure being partially released.

FIG. 24 shows a system for delivering the LAA closure according to a seventh embodiment of the present invention, with the LAA closure being partially released. As shown in FIG. 24, the system 9 according to this embodiment includes a first delivery member 90 and a second delivery member 91 inside the first delivery member 90. The first delivery member 90 may be coupled to or separated from the first hub 30 (of the LAA closure 3), and the second delivery member 91 may be coupled to or separated from the second hub 35 (of the LAA closure 3). Specifically, in order to load the LAA closure 3, the first delivery member 90 is coupled to the first hub 30 of the LAA closure 3 and the second delivery member 91 is coupled to the second hub 35 of the LAA closure 3 so that the LAA closure 3 can be crimped to allow the loading. This design can avoid an excessive length of the LAA closure 3 when it is loaded.

In this embodiment, the first delivery member 90 is flared at the distal end and the second delivery member 91 can be engaged with the second hub 35 by a threaded connection. The first delivery member 90 is fixed to the first hub 30 by abutting the first delivery member 90 to the first hub 30. Due to the flared portion of the first delivery member 90, when the second delivery member 91 is engaged with the second hub 35 by a threaded connection, the first delivery member 90 is abutted to the second hub 35, enabling the LAA closure 3 to be crimped.

Again, the delivery system 9 may also include a sheath, a stopper, a handle and other components (including those not specified in this embodiment) that are the same as the first embodiment. These components will not be detailed again here, and reference can be made to the first embodiment for their details.

The LAA closure 3 can be deployed as described below.

The first delivery member 90 and the second delivery member 91 are advanced within the sheath 92 so that a first portion of the LAA closure 3 is released (under the distal push of the first delivery member 90 and the second delivery member 91). At this point, repeated relocations and adjustments are possible. After the first portion is deployed in place, the threaded connection between the second delivery member 91 and the second hub 35 is loosened so that the LAA closure 3 covers the LAA 7. The first delivery member 90 is then retracted to completely deploy the LAA closure 3.

In summary, the system for delivering the LAA closure according to this embodiment can avoid an excessive length of the LAA closure when it is loaded in the sheath. Meanwhile, since repeated relocations during the deployment are possible, the LAA closure can be better loaded into and deployed from the sheath.

Embodiment 8

A system for delivering the LAA closure according to an eighth embodiment includes a first delivery member and a second delivery member inside the first delivery member. The first delivery member may be coupled to or separated from the first hub 30 (of the LAA closure 3), and the second delivery member may be coupled to or separated from the second hub 35 (of the LAA closure 3). Specifically, in order to load the LAA closure 3, the first delivery member 90 is coupled to the first hub 30 of the LAA closure 3 and the second delivery member 91 is coupled to the second hub 35 of the LAA closure 3 so that the LAA closure 3 can be crimped to allow the loading. This design can avoid an excessive length of the LAA closure 3 when it is loaded.

This embodiment differs from the fifth, sixth or seventh embodiment essentially in that the first hub can be engaged with the second hub.

Figure 25:
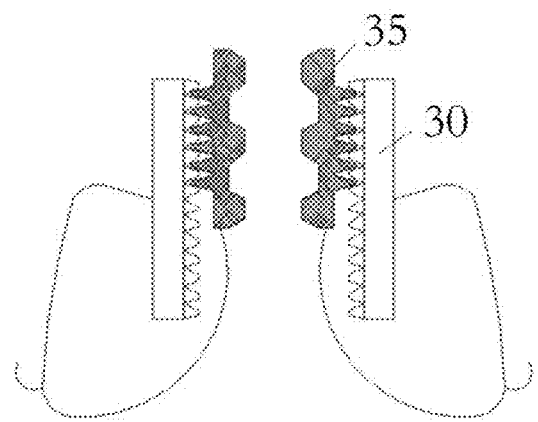
FIG. 25 schematically illustrates a system for delivering the LAA closure according to an eighth embodiment of the present invention subsequent to complete deployment of the LAA closure.
Figure 26:
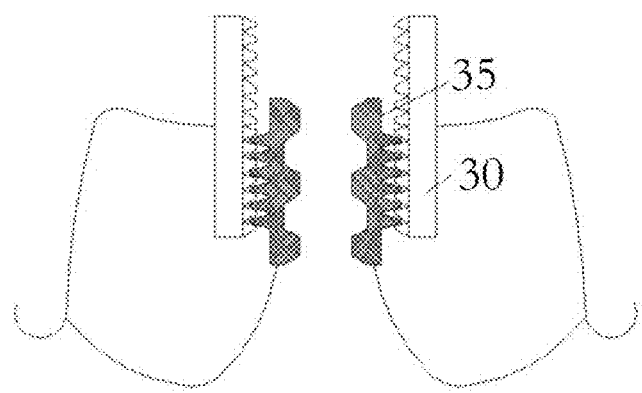
FIG. 26 schematically illustrates the system according to the eighth embodiment of the present invention in another configuration subsequent to complete deployment of the LAA closure.
Figure 27:
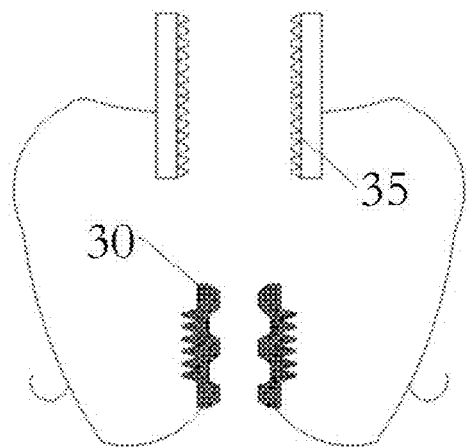
FIG. 27 schematically illustrates the system according to the eighth embodiment of the present invention in still another configuration subsequent to complete deployment of the LAA closure.

Specifically, reference can be made to FIGS. 25 and 26, in which FIG. 25 illustrates a schematic illustration of the system according to this embodiment, with the LAA closure having been completely deployed, and FIG. 26 illustrates a schematic illustration of the system according to this embodiment in another configuration, with the LAA closure having been completely deployed. As shown in FIGS. 25 and 26, after the LAA closure has been completely deployed, the first hub 30 may be partially or wholly engaged with the second hub 35. The partial or whole engagement of the first hub 30 and the second hub 35, coupled with the position of engagement, allows the LAA closure to be better adapted to the particular anatomical geometry of the LAA. Specifically, when the LAA is small in size, engagement of the second hub 35 with an upper portion of the first hub 30 (see FIG. 25) will result in a better adaptation of the LAA closure to the LAA. When the LAA is rather bulky, the LAA closure will be better adapted to the LAA when the second hub 35 is engaged with a lower portion of the first hub 30 (see FIG. 26). When the LAA is even bigger, the second hub 35 is desired to be disengaged from the first hub 30 (see FIG. 27) so that the LAA closure can be better adapted to the LAA.

Figure 28:
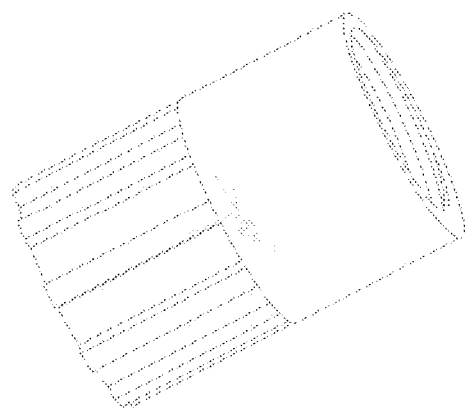
FIG. 28 shows external splines according to the eighth embodiment of the present invention.
Figure 29:
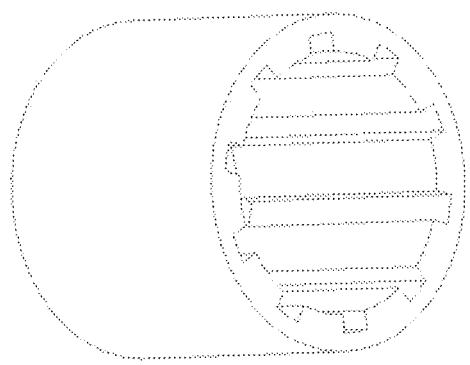
FIG. 29 shows internal splines according to the eighth embodiment of the present invention.
Figure 30:
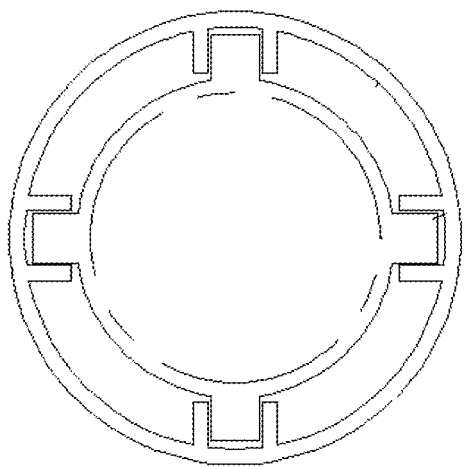
FIG. 30 shows the external and internal splines according to the eighth embodiment of the present invention that are connected together.

The first hub 30 may be engaged with the second hub 35 by a snap connection or by an internal/external spline connection. For example, the first hub 30 may be engaged with the second hub 35 by a snap connection (see FIGS. 25 to 27) including internal snapping lips on the first hub 30 and external snapping lips on the second hub 35. Alternatively, the first hub 30 may be engaged with the second hub 35 by an internal/external spline connection (see FIGS. 28 to 30) including internal spines on the first hub 30 and external splines on the second hub 35.

Further, the first hub 30 may have an external thread that can engage an internal thread on the first delivery member. Further, the second hub 35 may have an internal thread that can engage an external thread on the second delivery member.

As stated above, in each of the foregoing LAA closure delivery systems, before the LAA closure is loaded, the first delivery member is coupled to a first hub of the LAA closure and the second delivery member inside the first delivery member is coupled to a second hub thereof so that the LAA closure can be crimped to allow the loading. This design can avoid an excessive length of the LAA closure when it is loaded. In the deployment process, a second portion of the LAA closure with anchors is first released. At this point, repeated relocations are allowed until a suitable deployment site is reached. After that, the first and second hubs of the LAA closure are deployed. Therefore, the proposed systems make it possible for the LAA closure to be better loaded or deployed.

The description presented above is merely that of a few preferred embodiments of the present invention and does not limit the scope thereof in any sense. Any and all changes and modifications made by those of ordinary skill in the art based on the above teachings fall within the scope as defined in the appended claims.

What is claimed is:

1. A left atrial appendage (LAA) closure, comprising a plurality of supporting struts distributed peripherally around a first hub and extending outwardly from the first hub, the supporting strut bifurcating at a first position into a left branch and a right branch, the left branch of a supporting strut and the right branch of an adjacent supporting strut joining each other at a second position and extending distally to form a distal end, the LAA closure further comprising a supporting rod disposed between adjacent supporting struts.

2. The LAA closure according to claim 1, wherein the supporting rod has a first end connected to the outside of the first hub, extending outwardly and bifurcating into a second end and a third end at a third position.

3. The LAA closure according to claim 2, wherein the second end is fixed between the first and second positions of the left branch of the supporting struts, and the third end is fixed between the first and second positions of the right branch of the supporting struts.

4. The LAA closure according to claim 2, wherein the second and third ends are fixed on two adjacent supporting struts.

5. The LAA closure according to claim 2, wherein a length of the supporting rod from the first hub to the third position is smaller than a length of the supporting strut from the first hub to the first position.

6. The LAA closure according to claim 2, wherein some or all of the supporting struts comprise a barb, and/or some or all of the left and right branches comprise a barb.

7. The LAA closure according to claim 1, wherein the left and right branches of the same supporting strut are connected to each other at the distal ends thereof.

8. The LAA closure according to claim 7, wherein each of the distal ends is bent toward the proximal end to form an anchor.

9. The LAA closure according to claim 8, wherein a length from the point where the distal end starts bending to a final point of the distal end is greater than a length from a junction of the distal ends to the final point.

10. The LAA closure according to claim 1, wherein the distal ends extend inwardly to form a second hub.

11. The LAA closure according to claim 1, wherein the distal ends protrude radially to form an anchor.

* * * * *